US011931005B2

(12) United States Patent
Naito et al.

(10) Patent No.: US 11,931,005 B2
(45) Date of Patent: Mar. 19, 2024

(54) DRIVING FORCE TRANSMISSION MECHANISM FOR ENDOSCOPE AND ENDOSCOPE

(71) Applicant: OLYMPUS CORPORATION, Tokyo (JP)

(72) Inventors: Kimihiko Naito, Kawasaki (JP); Hiroaki Miyoshi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 666 days.

(21) Appl. No.: 17/093,906

(22) Filed: Nov. 10, 2020

(65) Prior Publication Data

US 2021/0100430 A1 Apr. 8, 2021

Related U.S. Application Data

(63) Continuation of application No. PCT/JP2019/007102, filed on Feb. 25, 2019.

(30) Foreign Application Priority Data

May 16, 2018 (JP) ................................ 2018-094720

(51) Int. Cl.
*A61B 1/00* (2006.01)
*A61B 1/005* (2006.01)

(52) U.S. Cl.
CPC .......... *A61B 1/0057* (2013.01); *A61B 1/0055* (2013.01)

(58) Field of Classification Search
CPC ....... A61B 1/0057; A61B 1/0055; A61B 1/00; A61B 1/0016; A61B 1/00133; A61B 1/00156
USPC ........................................................ 600/137
See application file for complete search history.

(56) References Cited

U.S. PATENT DOCUMENTS

2017/0224195 A1   8/2017   Kubo

FOREIGN PATENT DOCUMENTS

| EP | 3 199 089 A1 | 8/2017 |
| JP | 09-300414 A | 11/1997 |
| JP | 10-159836 A | 6/1998 |
| JP | 6072390 B1 | 2/2017 |

OTHER PUBLICATIONS

International Search Report dated Apr. 23, 2019 received in PCT/JP2019/007102.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A driving force transmission mechanism for an endoscope includes an insertion portion, an operation portion, an electric motor, an output member, a rotation transmission member, an inside plane, a first plane, a second plane and a third plane configured to come into contact with a proximal end of the output member when at least part of the second plane comes into contact with the inside plane to thereby restrict the rotation transmission member from moving toward the distal end side in the axial direction with respect to the output member.

18 Claims, 8 Drawing Sheets

DRIVING FORCE TRANSMISSION MECHANISM FOR ENDOSCOPE AND ENDOSCOPE

CROSS REFERENCE TO RELATED APPLICATION

This application is a continuation application of PCT/JP2019/007102 filed on Feb. 25, 2019, and claims benefit of Japanese Application No. 2018-094720 filed in Japan on May 16, 2018, the entire contents of which are incorporated herein by this reference.

BACKGROUND OF THE INVENTION

1. Field of the Invention

The present invention relates to a driving force transmission mechanism for an endoscope in which an output member transmits rotation of a drive source to a rotation transmission member, and the endoscope.

2. Description of the Related Art

In recent years, endoscopes have been widely used in the medical field. Endoscopes used in the medical field can observe a site to be examined in a body cavity through insertion of an insertion portion that is formed so as to extend long in an axial direction into the body cavity.

In order to improve observability and treatment performance of the site to be examined in the body cavity by an observation optical system provided for the endoscope, a power spiral endoscope is well known, which includes a spiral structure, which is an external instrument, provided on an outer circumference on a distal end side in an axial direction of the insertion portion.

Note that the spiral structure includes a spiral protrusion on an outer circumferential surface in an axial direction and is configured to be rotatable around a rotation shaft parallel or substantially parallel to the axial direction.

The protrusion of the power spiral endoscope comes into contact with an inner wall of the body cavity while rotating, to thereby produce a propelling force at the insertion portion and draw the site to be examined in the body cavity located apart from the observation optical system provided at the distal end of the insertion portion toward a proximity position of the observation optical system.

This makes it possible to improve observability of the observation optical system and treatment performance of the endoscope.

Japanese Patent No. 6072390 discloses a configuration of a power spiral endoscope that rotates a spiral structure around a rotation shaft.

The power spiral endoscope in Japanese Patent No. 6072390 transmits rotation of an electric motor, which is a drive source, provided inside a proximal end portion of the insertion portion or inside the operation portion to a flexible torque shaft provided inside the insertion portion via gears. The power spiral endoscope is configured to transmit rotation of the electric motor to the spiral structure via gears, which are driven member, provided at the distal end of the torque shaft.

In the power spiral endoscope disclosed in Japanese Patent No. 6072390, an output member rotatable together with the gears is connected to the gears and a rotation transmission member connected to the proximal end of the torque shaft is inserted into a through hole formed in the axial direction with respect to the output member.

This provides a configuration in which rotation of the electric motor is transmitted to the spiral structure via the gears, the output member, the rotation transmission member, the torque shaft and the gear.

In the power spiral endoscope disclosed in Japanese Patent No. 6072390, since the torque shaft is provided inside the insertion portion as described above, the torque shaft is made of a flexible member so as not to obstruct flexibility of the insertion portion.

More specifically, the torque shaft is constructed of a plurality of layers and configured to transmit rotation of the output member not only in one of rotation directions toward the gear but also in another direction, providing a configuration in which flexible right-handed and left-handed coils are alternately stacked.

In addition, the gear is fixed to the distal end of the torque shaft and the axial position of the gear is fixed.

For this reason, when the spiral structure is rotated in the one direction to draw the site to be examined, the torque shaft contracts in the axial direction of the insertion portion together with the rotation transmission member.

When the torque shaft is rotated in the other direction opposite to the one direction, the torque shaft has a characteristic that the overall length changes in the axial direction with the torque shaft extending in the axial direction of the insertion portion together with the rotation transmission member.

SUMMARY OF THE INVENTION

A driving force transmission mechanism for an endoscope according to one aspect of the present invention includes an insertion portion that is formed so as to extend long in an axial direction and configured to be inserted into an object, an operation portion continuously provided on a proximal end side in the axial direction of the insertion portion, a drive source disposed at a proximal end portion in the axial direction of the insertion portion or in the operation portion, an output member that is driven by the drive source to rotate around a rotation shaft parallel or substantially parallel to the axial direction of the insertion portion and includes a through hole along the rotation shaft, a rotation transmission member that is inserted into the through hole of the output member from a distal end side in the axial direction of the through hole and configured to receive a rotation driving force around the rotation shaft along with the rotation of the output member, an inside plane that is provided on an inner surface of the through hole in the output member and formed so as to extend parallel to the rotation shaft, a first plane that is provided so as to extend to a proximal end in the axial direction parallel to the rotation shaft on an outer circumferential surface of the rotation transmission member and part of the first plane faces the inside plane of the output member when the rotation transmission member is inserted into the through hole of the output member, a second plane that is provided on the outer circumferential surface of the rotation transmission member and formed parallel to the rotation shaft and inclined with respect to the first plane so as to extend by a set distance from a position closer to the distal end side in the axial direction than the proximal end in the axial direction of the rotation transmission member to a distal end side in the axial direction, and at least part of the second plane comes into contact with the inside plane during rotation of the output member to receive the rotation force of the output member and a third plane that is formed so as to connect a proximal end in the axial direction of the second plane and the first plane of the rotation transmission member and comes into contact with a proximal end in the axial direction of the output member when the output member rotates with respect to the rotation transmission member and at least part of the second plane contacts the inside plane, to thereby restrict the rotation transmission member from moving toward the distal end side in the axial direction with respect to the output member.

A driving force transmission mechanism for an endoscope according to another aspect of the present invention includes an output member that is driven by a drive source to rotate around a rotation shaft and includes a through hole along the rotation shaft, a rotation transmission member that is inserted into the through hole of the output member from one side of the rotation shaft and configured to receive a rotation driving force around the rotation shaft in a same direction as a direction of the rotation of the output member with the rotation of the output member, an inside plane that is provided on an inner surface of the through hole in the output member and formed so as to extend parallel to the rotation shaft, a first plane that is provided so as to extend to another end in an extending direction of the rotation shaft parallel to the rotation shaft on an outer circumferential surface of the rotation transmission member and part of the first plane faces the inside plane of the output member when the rotation transmission member is inserted into the through hole of the output member, a second plane that is provided on the outer circumferential surface of the rotation transmission member and formed parallel to the rotation shaft and inclined with respect to the first plane so as to extend by a set distance from a position closer to one end of the rotation transmission member in the extending direction than the other end of the rotation transmission member to a one end side of the rotation transmission member, and at least part of the second plane comes into contact with the inside plane during rotation of the output member to receive the rotation force of the output member and a third plane that is formed so as to connect an end face of the second plane on the other end side of the rotation shaft and the first plane and comes into contact with an end portion on the other end side in the extending direction of the output member when the output member rotates with respect to the rotation transmission member and at least part of the second plane contacts the inside plane, to thereby restrict the rotation transmission member from moving toward the one end side with respect to the output member.

Furthermore, an endoscope according to one aspect of the present invention includes the driving force transmission mechanism for an endoscope.

DETAILED DESCRIPTION OF THE PREFERRED EMBODIMENT

Hereinafter, an embodiment of the present invention will be described with reference to the accompanying drawings. Note that in order to illustrate each component in a size recognizable on the drawings, the scale of each component may differ from one component to another. In other words, the present invention is not limited to a quantity of each component, a shape of each component, a size ratio among components and relative positional relationship among the components alone.

Figure 1:
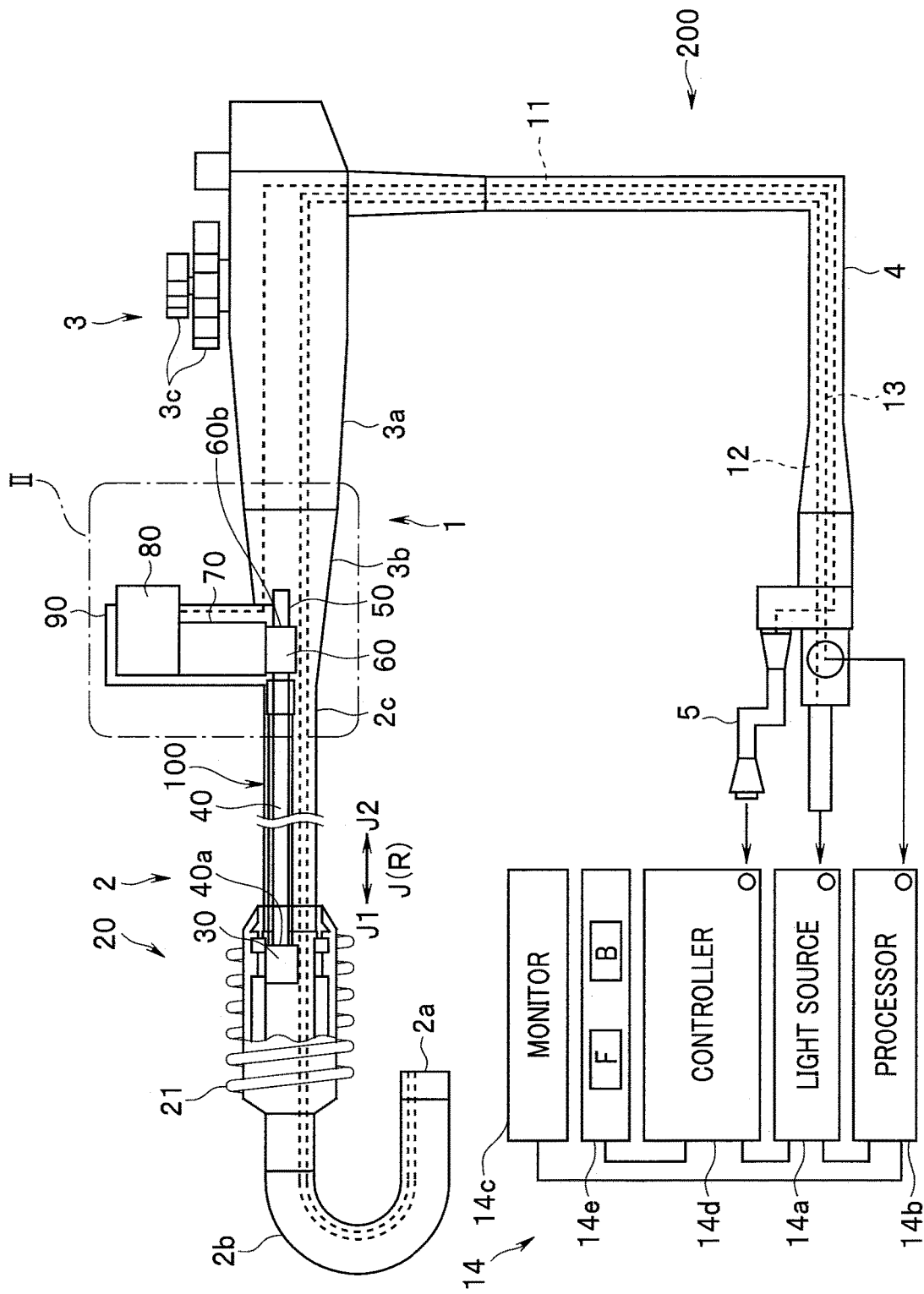
FIG. 1 is a diagram illustrating an overview of a configuration of an endoscope system provided with an endoscope including a driving force transmission mechanism of the present embodiment.
Figure 2:
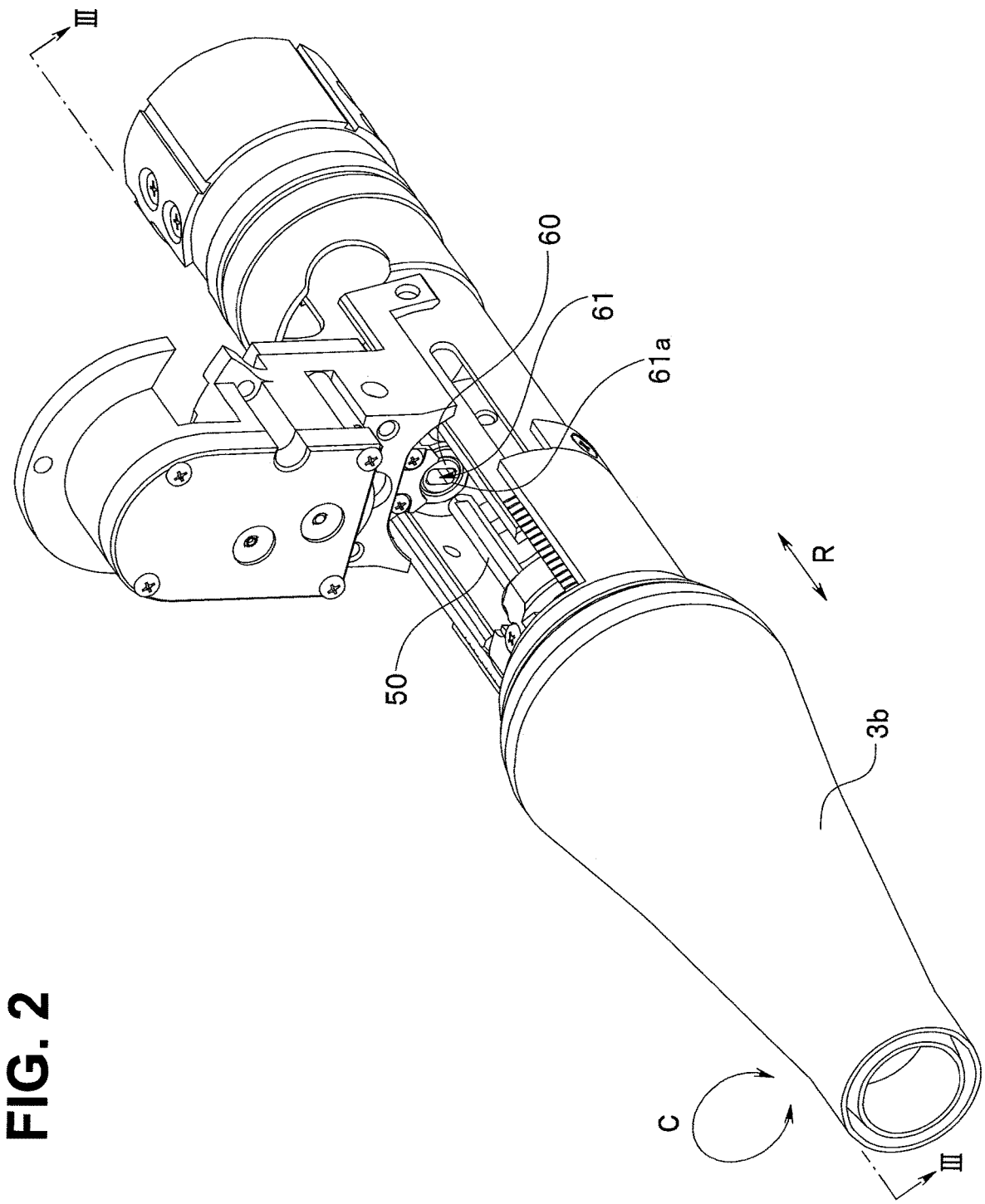
FIG. 2 is an enlarged perspective view of a region enclosed with a line II in FIG. 1 of the endoscope in FIG. 1.
Figure 3:
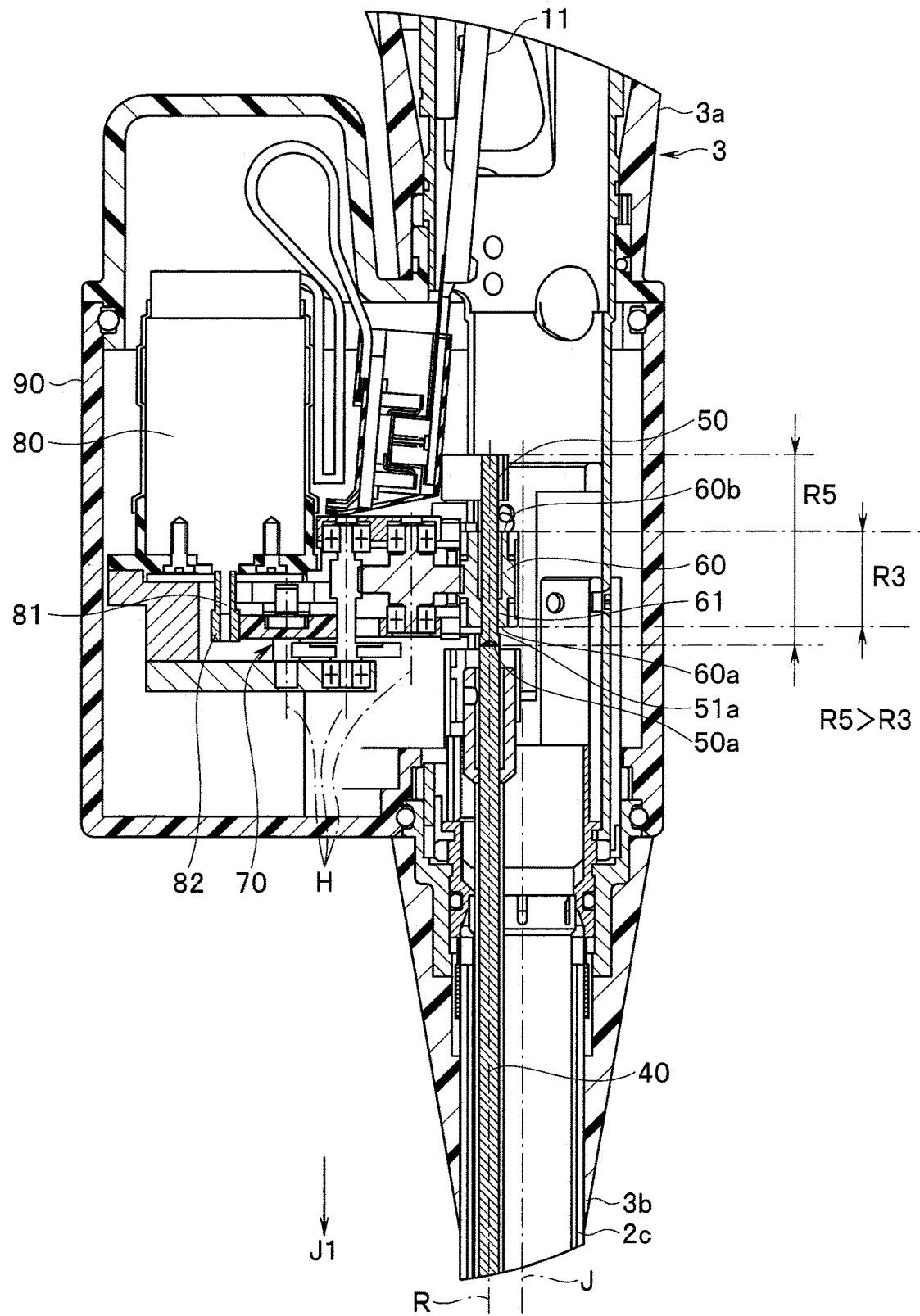
FIG. 3 is a partial cross-sectional view of the endoscope along a line in FIG. 2.

FIG. 1 is a diagram illustrating an overview of a configuration of an endoscope system provided with an endoscope including a driving force transmission mechanism of the present embodiment, FIG. 2 is an enlarged perspective view of a region enclosed with a line II in FIG. 1 of the endoscope in FIG. 1 and FIG. 3 is a partial cross-sectional view of the endoscope along a line in FIG. 2.

As illustrated in FIG. 1, an endoscope system 200 is constructed of an endoscope 1 and a control system 14 connected to the endoscope 1 as main parts.

The endoscope 1 is constructed of an insertion portion 2, which is formed long so as to extend in an axial direction J and configured to be inserted into an object, an operation portion 3 continuously provided on a proximal end side J2, which is another side of the axial direction J of the insertion portion 2 (hereinafter simply referred to as "proximal end side J2"), a universal cord 4 extending from the operation portion 3 and a connector 5 detachably attached to a control system 14 provided at an extending end of the universal cord 4 as main parts.

An observation optical system 13 constructed of a light guide 12, an image pickup unit (not shown) and an image pickup cable is inserted into the insertion portion 2, the operation portion 3, the universal cord 4 and the connector 5.

Furthermore, a motor power cable 11 is inserted into the operation portion 3, the universal cord 4 and the connector 5.

The insertion portion 2 is constructed of a distal end portion 2a provided at a distal end in the axial direction J (hereinafter simply referred to as "distal end"), a bending portion 2b connected to a proximal end in the axial direction J (hereinafter simply referred to as "proximal end") of the distal end portion 2a and bendable in a plurality of directions, and a flexible tube portion 2c connected to a proximal end of the bending portion 2b and provided with flexibility.

The operation portion 3 is constructed of a grasping portion 3a and a bending stopper 3b as main parts.

The grasping portion 3a is provided with bending operation knobs 3c that are operated by an operator to bend the bending portion 2b in a plurality of directions and various operation switches (not shown) of the endoscope 1.

The bending stopper 3b is connected to a distal end of the grasping portion 3a and also connected to the proximal end 2c of the flexible tube portion 2c to prevent the flexible tube portion 2c from bending.

The control system 14 is constructed of a light source 14a, a processor 14b, a monitor 14c, a controller 14d and an input switch 14e as main parts.

The light source 14a is configured to supply illumination light into an object via the light guide 12.

The processor 14b performs image processing so that an image of an interior of the object picked up by an image pickup unit (not shown) of the observation optical system 13 is displayed on the monitor 14c.

Furthermore, in addition to driving/controlling the whole endoscope system 200, the controller 14d drives/controls an electric motor 80, which will be described later and to which the motor power cable 11 is electrically connected, via the motor power cable 11.

The input switch 14e is constructed of a keyboard and a foot switch or the like, and configured to allow the operator to input an instruction for driving the electric motor 80 to the controller 14d.

Here, a driving force transmission mechanism 100 is provided inside the insertion portion 2 and the operation portion 3. The driving force transmission mechanism 100 is constructed of an electric motor 80, which is a drive source, at least one gear 70, a casing 90 configured to house the gear 70 and the electric motor 80, an output member 60, a rotation transmission member 50, a torque shaft 40, a gear 30, which is a driven member and a spiral structure 20, which is an external device, as main parts.

According to the present embodiment, the electric motor 80 is provided inside the casing 90 connected to the bending stopper 3b of the operation portion 3. Note that the casing 90 may also be connected to a proximal end side of the flexible tube portion 2c.

The motor power cable 11 is electrically connected to the electric motor 80. When input is made from the input switch 14e to the controller 14d, the electric motor 80 causes an output shaft 81 and a gear 82 provided at the output shaft 81 (see FIG. 3) to rotate in a direction C around a rotation shaft, which will be described later.

Note that the electric motor 80 is provided such that the output shaft 81 and the gear 82 inside the casing 90 point to a distal end side J1 which is one side in the axial direction J (hereinafter simply referred to as "distal end side J1").

As illustrated in FIG. 3, the gear 70 is meshed with the gear 82. The gear 70 is interposed between the gear 82 and the output member 60.

Note that although a case has been described as an example in FIG. 3 where the gear 70 is constructed of a plurality of gears, the gear 70 may be constructed of one gear.

A rotation shaft H of the gear 70 is disposed parallel or substantially parallel to an extending direction R of the rotation shaft of the output shaft 81 or the output member 60.

Note that the extending direction R of the rotation shaft is also disposed parallel or substantially parallel to the output shaft 81. The extending direction R of the rotation shaft is parallel or substantially parallel to the axial direction J.

In the output member 60, a gear (not shown) formed on the outer circumferential surface is meshed with the gear 70. The output member 60 receives a rotation force transmitted from the electric motor 80 via the output shaft 81, the gear 82 and the gear 70, and therefore the electric motor 80 drives the output member 60 to rotate in a direction C around the extending direction R of the rotation shaft.

As illustrated in FIG. 2 and FIG. 3, the output member 60 is formed to a length of R3 in the extending direction R of the rotation shaft and a through hole 61 having a length of R3 is formed inside from a distal end 60a to a proximal end 60b in the extending direction R of the rotation shaft.

The rotation transmission member 50 has a length of R5 longer than the through hole 61 in the axial direction J (R5>R3).

The rotation transmission member 50 is slidably inserted into the through hole 61 in the extending direction R of the rotation shaft from the distal end side J1 and the rotation of the output member 60 causes a rotation driving force in the same rotation direction as the rotation direction of the output member 60 in the direction C around the rotation shaft to be transmitted from the output member 60.

As illustrated in FIG. 1 and FIG. 3, the torque shaft 40 is coupled with a distal end 50a, which is one end of the rotation transmission member 50 coaxially with the rotation transmission member 50 and rotates in the same direction C around the rotation shaft of the rotation transmission member 50.

Though not illustrated, the torque shaft 40 is constructed of a plurality of layers and is configured to transmit the rotation of the output member 60 to the gear 30 not only in the one direction C1 but also in another direction C2 and so has a well-known configuration in which flexible right-handed and left-handed coils are alternately stacked.

Note that the torque shaft 40 is assembled by being slightly pushed and bent toward the distal end of the insertion portion 2. The presence of bending in the torque shaft 40 prevents the proximal end portion of the torque shaft 40 from being pulled in toward the insertion portion 2 side even when the insertion portion 2 is extremely bent or the whole insertion portion 2 forms a loop shape so that the coupling between the rotation transmission member 50 and the output member 60 is always maintained.

The gear 30 is coupled with the distal end 40a of the torque shaft 40 and rotates around the rotation shaft in the direction C, the same as the direction of the torque shaft 40. In other words, the torque shaft 40 drives the gear 30. The position in the axial direction J of the gear 30 is fixed.

The spiral structure 20 is provided, for example, on an outer circumference of the distal end of the flexible tube portion 2c and caused by the gear 30 to rotate around the rotation shaft in the direction C, the same as the direction of the gear 30. Note that the position of the flexible tube portion 2c at which the spiral structure 20 is provided is not limited to the position illustrated in FIG. 1. Moreover, the spiral structure 20 may also be provided on an outer circumference of the distal end portion 2a.

As illustrated in FIG. 1, the spiral structure 20 includes a spiral protrusion 21 in the axial direction J on the outer circumferential surface.

With the protrusion 21 contacting the inner wall of the body cavity, which is an object, while rotating, the spiral structure 20 produces a propelling force at the insertion portion 2 or draws in a site to be examined in the body cavity located apart from the distal end portion 2a to a proximity position of the distal end portion 2a. This improves observability of the observation optical system 13 and treatment performance of the endoscope 1.

Note that the torque shaft 40 has a characteristic that the overall length of the torque shaft 40 changes in the axial direction J, for example, when the spiral structure 20 is rotated in the one direction C1 to draw in the site to be examined, the torque shaft 40 contracts in the axial direction J together with the rotation transmission member 50 or when the spiral structure 20 is rotated in the other direction C2, the torque shaft 40 extends in the axial direction J together with the rotation transmission member 50.

Next, detailed configurations of the through hole 61 of the output member 60 and the rotation transmission member 50 will be described using FIG. 4 to FIG. 6.

Figure 4:
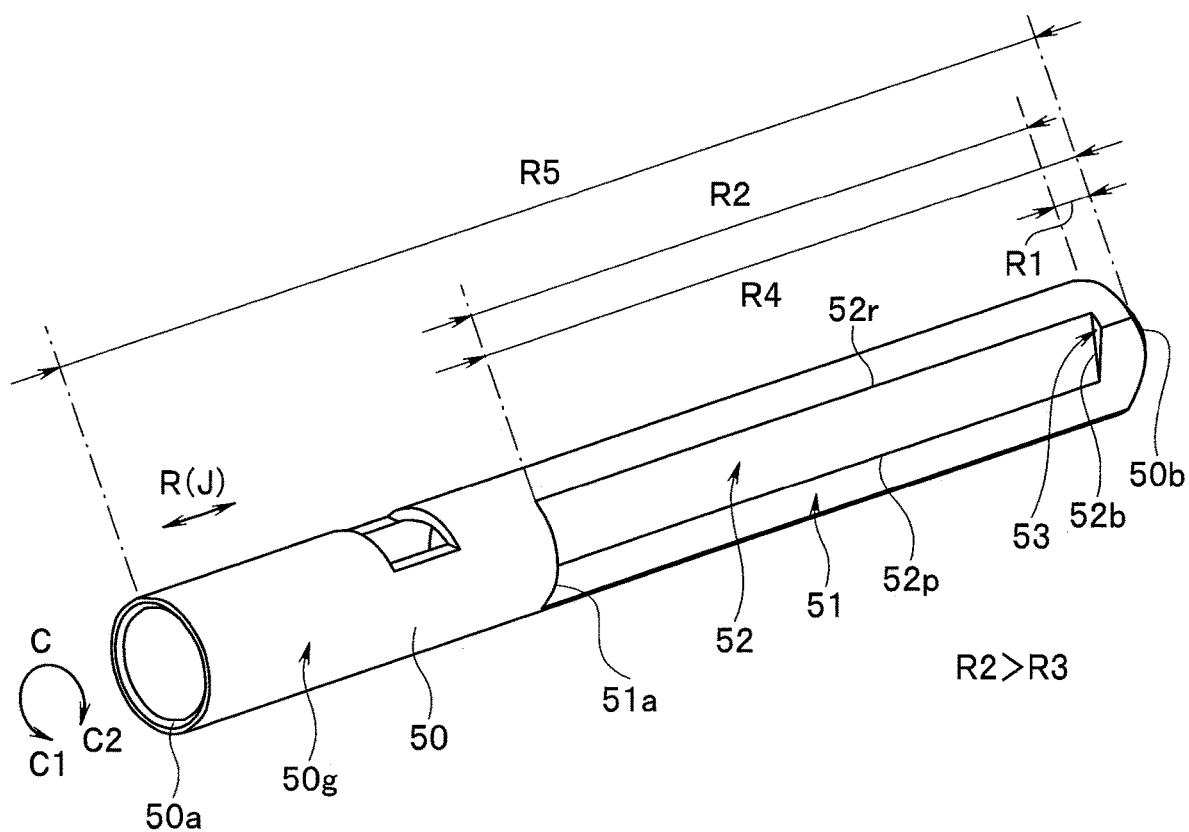
FIG. 4 is an enlarged perspective view of the rotation transmission member in FIG. 3.
Figure 5:
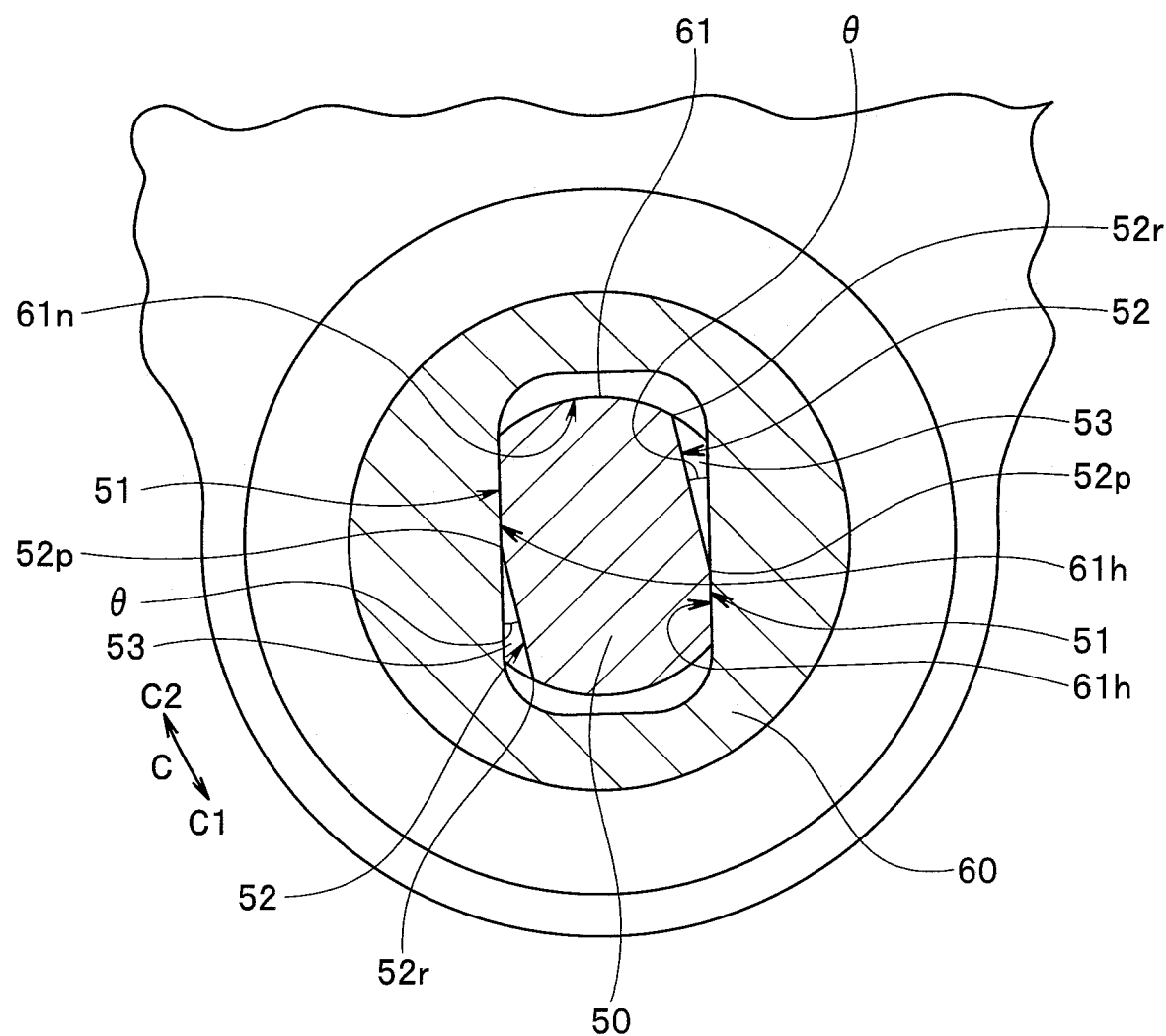
FIG. 5 is a partial cross-sectional view of the output member and the rotation transmission member along a line V-V in FIG. 3 as main parts.
Figure 6:
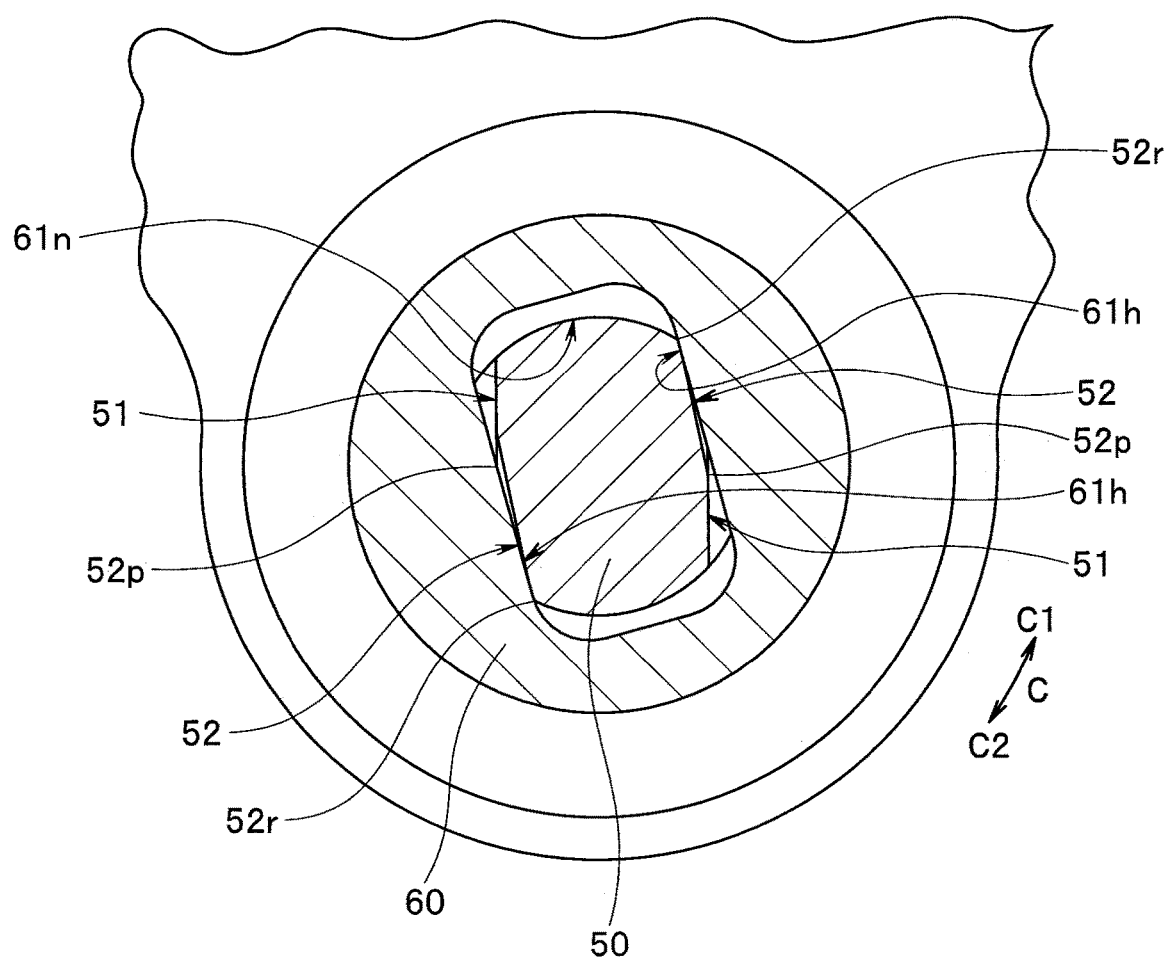
FIG. 6 is a partial cross-sectional view illustrating a state in which the output member in FIG. 5 rotates in one direction and an inside plane of a through hole is in contact with part of the rotation transmission member.

FIG. 4 is an enlarged perspective view of the rotation transmission member in FIG. 3, FIG. 5 is a partial cross-sectional view of the output member and the rotation transmission member along a line V-V in FIG. 3 as main parts and FIG. 6 is a partial cross-sectional view illustrating a state in which the output member in FIG. 5 rotates in one direction and an inside plane of the through hole is in contact with part of the rotation transmission member.

As illustrated in FIG. 5 and FIG. 6, the through hole 61 formed in the output member 60 includes a pair of inside planes 61h that are rectilinearly formed so as to extend parallel to the extending direction R of the rotation shaft on an inner surface 61n.

In other words, the through hole 61 is formed to have a substantially oval cross-sectional shape including a pair of opposing rectilinear inside planes 61h.

As illustrated in FIG. 4 to FIG. 6, a pair of opposing first planes 51 are formed on an outer circumferential surface 50g of the rotation transmission member 50 parallel to the extending direction R of the rotation shaft so as to extend over a length of R4 from a half part in the axial direction J of the rotation transmission member 50 to the proximal end 50b.

When the rotation transmission member 50 is inserted into the through hole 61, part of the first plane 51 faces the inside planes 61h, and the first plane 51 functions as a guide to allow insertion of the rotation transmission member 50 into the through hole 61.

When the output member 60 rotates in the other direction C2, the inside planes 61h come into contact with the first plane 51 and the first plane 51 also has a function to transmit a rotation driving force in the other direction C2 to the rotation transmission member 50.

A pair of opposing second planes 52 are formed so as to extend toward the distal end side J1 by a set distance R2 from a position closer to the distal end side J1 by R1 than the proximal end 50b in the axial direction J on the outer circumferential surface 50g.

Note that the set distance R2 is formed slightly longer than the length R3 in the axial direction J of the through hole 61 (R2>R3).

The second plane 52 is formed inclined by an angle θ so as to be parallel to the extending direction R of the rotation shaft and so that one end portion 52r in the axial direction J is positioned closer to the center side in the extending direction R of the rotation shaft of the rotation transmission member 50 than the other end portion 52p with respect to the first plane 51.

While the rotation transmission member 50 is inserted into the through hole 61 so that the first plane 51 of the rotation transmission member 50 faces the inside planes 61h, the second plane 52 receives a rotation force of the output member 60 during rotation of the output member 60 in the one direction C1 when at least part of the rotation transmission member 50, or more specifically, the one end portion 52r contacts the inside planes 61h in the axial direction J.

Note that as a matter of course, a configuration in which the inside planes 61h contact the whole second plane 52 may also be adopted. In this way, the rotation transmission member 50 rotates in the one direction C1 along with the output member 60.

Furthermore, a pair of third planes 53 are formed so as to connect the proximal end 52b, which is an end face of the proximal end side J2 of the second plane 52 and the first plane 51 of the rotation transmission member 50. A receiving surface 51a is also provided to connect the end face on the distal end side of the first plane 51 and the outer circumferential surface of the rotation transmission member 50.

As described above, when the torque shaft 40 is pushed in the insertion portion and assembled, the proximal end portion of the torque shaft 40 is pushed back from the insertion portion, but when the receiving surface 51a abuts on the end face on the insertion portion side of the output member 60, the torque shaft 40 can be kept pushed in the insertion portion.

When the inside plane 61h contacts the one end portion 52r of the second plane 52, the third plane 53 faces or abuts on the proximal end 60b of the output member 60 as illustrated in FIG. 3.

In this way, when the rotation transmission member 50 rotates in the one direction C1, the third plane 53 prevents the rotation transmission member 50 from coming off the through hole 61 toward the distal end side J1 along with contraction of the torque shaft 40 in the axial direction J as described above. In other words, the third plane 53 functions as a stopper to prevent the rotation transmission member 50 from coming off the through hole 61.

Note that when the output member 60 rotates in the other direction C2, the torque shaft 40 extends in the axial direction J as described above, but the position in the axial direction J of the gear 30 provided at the distal end 40a of the torque shaft 40 is fixed. This prevents the rotation transmission member 50 from coming off the through hole 61 toward the proximal end side J2, and so the aforementioned stopper using the third plane 53 is unnecessary.

Note that the rest of the configuration of the driving force transmission mechanism 100 is the same as the conventional configuration.

Thus, it has been shown in the present embodiment that the first plane 51 that functions as a guide when the rotation transmission member 50 is inserted into the through hole 61 is formed on the outer circumferential surface 50g of the rotation transmission member 50, which is inserted into the through hole 61 of the output member 60.

It has also been shown that when the rotation transmission member 50 rotates in the one direction C1, the second plane 52 with which the inside plane 61h of the through hole 61 comes into contact is formed on at least part of the outer circumferential surface 50g.

It has been further shown that when the rotation transmission member 50 rotates in the one direction C1, the third plane 53 that functions as a stopper for preventing the rotation transmission member 50 from coming off the through hole 61 toward the distal end side J1 when the torque shaft 40 contracts toward the distal end side J1.

Accordingly, when the output member 60 rotates in the one direction C1 by driving the electric motor 80, only by allowing insertion of the rotation transmission member 50 into the through hole 61 so that the first plane 51 faces the inside planes 61h using the first plane 51 as a guide, the inside planes 61h contacts at least part of the second plane 52. This allows the rotation transmission member 50, the torque shaft 40, the gear 30 and the spiral structure 20 to rotate in the one direction C1.

Even when the output member 60 is rotating in the one direction C1 together with the rotation transmission member 50 while in contact with at least part of the second plane 52, the third plane 53 is free to contact the proximal end 60b of the output member 60, and so it is possible to prevent the rotation transmission member 50 from coming off the through hole 61 toward the distal end side J1.

Thus, the third plane 53 functions as a coming-off stopper for the rotation transmission member 50, and so it is not necessary to form the rotation transmission member 50 long in the axial direction J or use a separate coming-off stopper in the conventional manner. It is possible to thereby prevent the endoscope 1 from becoming large, and it is possible not only to prevent workability during assembly or repairs from reducing but also to reduce manufacturing and repair costs.

For above reasons, assembly and repairs can be performed with high workability and it is possible to provide the driving force transmission mechanism 100 for an endoscope and the endoscope 1 configured to be able to reliably prevent the rotation transmission member 50 from coming off the through hole 61 of the output member 60 during rotation with a simple configuration that prevents increase in size.

Figure 7:
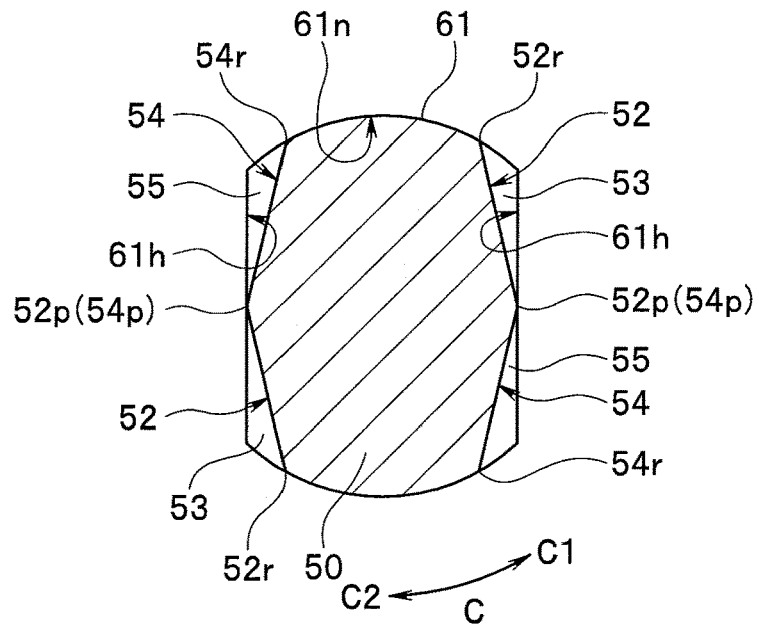
FIG. 7 is a partial cross-sectional view illustrating a modification in which a fourth plane is further provided on an outer circumferential surface of the rotation transmission member together with a through hole.
Figure 8:
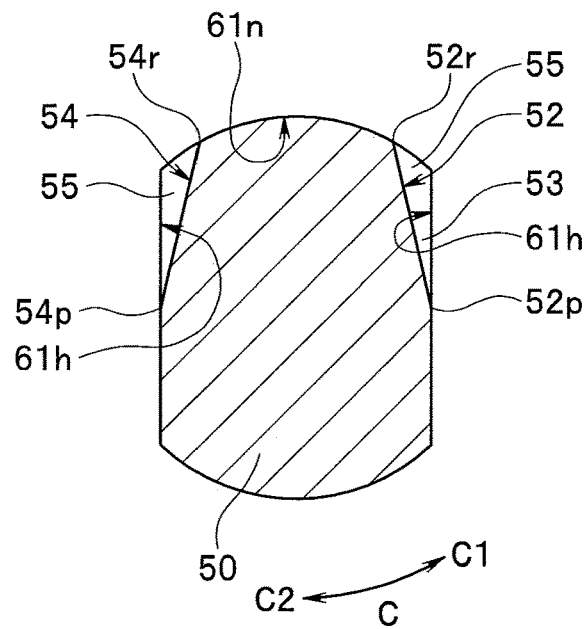
FIG. 8 is a partial cross-sectional view illustrating a modification in which a second plane and a fourth plane formed on the outer circumferential surface of the rotation member in FIG. 7 are formed from one plane each together with the through hole.

Note that modifications will be described using FIG. 7 and FIG. 8 hereinafter. FIG. 7 is a partial cross-sectional view illustrating a modification in which a fourth plane is further provided on an outer circumferential surface of the rotation transmission member together with a through hole and FIG. 8 is a partial cross-sectional view illustrating a modification in which a second plane and a fourth plane formed on the outer circumferential surface of the rotation member in FIG. 7 are formed from one plane each together with the through hole.

As described above, according to the present embodiment, when the output member 60, the rotation transmission member 50 and the torque shaft 40 rotate in the other direction C2, the torque shaft 40 extends toward the proximal end side J2, thus preventing the rotation transmission member 50 from coming off the through hole 61.

However, depending on the configuration of the torque shaft 40, if the torque shaft 40 rotates in the other direction C2, the torque shaft 40 may extend toward the distal end side J1, and for this reason, there may be cases where it is desirable to prevent the rotation transmission member 50 from coming off the through hole 61 toward the proximal end side J2 even during rotation in the one direction C1.

In these cases, as illustrated in FIG. 7, a pair of fourth planes 54 may be formed inclined so that the one end portion 54r in the axial direction J is located closer to the center side in the extending direction R of the rotation shaft of the rotation transmission member 50 than the other end portion 54p in a direction opposite to the second plane 52 with respect to the first plane 51 on the outer circumferential surface 50g in addition to the aforementioned pair of second planes 52.

Note that as illustrated in FIG. 8, the second plane 52 and the fourth plane 54 may be formed from one plane each.

In this case, if the output member 60 rotates in the other direction C2, the inside planes 61h transmit a rotation force toward the other direction C2 in contact with at least part of the fourth plane 54 to the rotation transmission member 50 via the fourth plane 54.

Furthermore, when preventing the rotation transmission member 50 from coming off toward the proximal end side J2, a fifth plane 55 formed so as to face the third plane 53 in the axial direction J and connect the first plane 51 and the fourth plane 54 functions as a coming-off stopper.

When the torque shaft 40 extends toward the distal end side J1 as the rotation transmission member 50 rotates in the one direction C1, the third plane 53 functions as a coming-off stopper for the rotation transmission member 50 in the same way as in the aforementioned present embodiment.

With such a configuration, it is also possible to obtain effects similar to the effects of the aforementioned present embodiment regardless of the rotating direction of the rotation transmission member 50.

Figure 9:
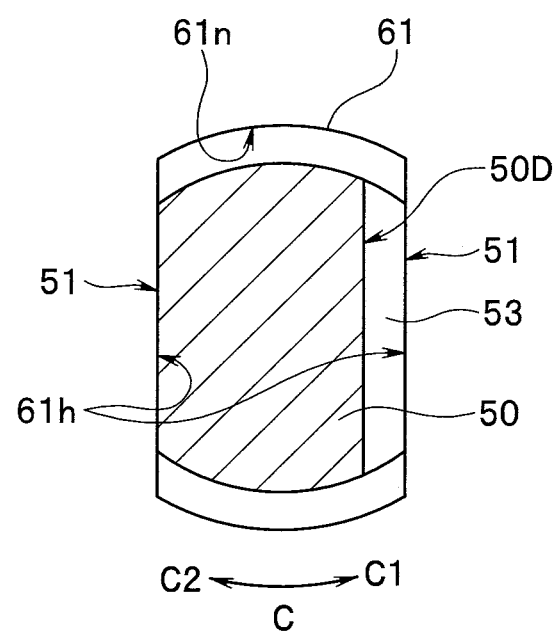
FIG. 9 is a partial cross-sectional view illustrating a modification in which a D cut portion is formed on the outer circumferential surface of the rotation transmission member together with the through hole.

Another modification will be described hereinafter using FIG. 9. FIG. 9 is a partial cross-sectional view illustrating a modification in which a D cut portion is formed on the outer circumferential surface of the rotation transmission member together with the through hole.

As illustrated in FIG. 9, a D cut portion 50D may also be formed on the outer circumferential surface 50g of the rotation transmission member 50 instead of the second plane 52 and the fourth plane 54 in addition to the first plane 51 and the third plane 53.

According to such a configuration, the inside planes 61h come into contact with the D cut portion 50D regardless of the one direction C1 or the other direction C2.

For this reason, the third plane 53 can prevent the rotation transmission member 50 from coming off the through hole 61 and only providing the one D cut portion 50D can reliably transmit rotation of the output member 60 in the directions R1 and R2 to the rotation transmission member 50, and it is therefore possible to obtain effects similar to the effects in the aforementioned present embodiment and modifications.

The present invention is not limited to the aforementioned embodiment, but can be changed as appropriate without departing from the gist or thought of the present invention that can be read from the scope of claims and the whole description, and an insertion instrument and an endoscope with such changes are also included in the technical scope of the present invention.

What is claimed is:

1. A driving force transmission mechanism for use with an endoscope, the driving force transmission mechanism comprising:
    an insertion portion extending in an axial direction and configured to be inserted into an object;
    an operation portion provided proximally relative to the insertion portion;
    a motor disposed at one of a proximal end portion in the axial direction of the insertion portion or in the operation portion;
    an output member driven by the motor to rotate around a rotation shaft parallel or substantially parallel to the axial direction of the insertion portion the output member including a through hole along the rotation shaft;
    a rotation transmission member inserted into the through hole of the output member from a distal end side in the axial direction of the through hole and configured to receive a rotation driving force around the rotation shaft along with a rotation of the output member;
    an inside plane provided on an inner surface of the through hole in the output member, the inside plane extending parallel to the rotation shaft;
    a first plane extending to a proximal end in the axial direction parallel to the rotation shaft on an outer circumferential surface of the rotation transmission member and part of the first plane faces the inside plane of the output member when the rotation transmission member is inserted into the through hole of the output member;

a second plane provided on the outer circumferential surface of the rotation transmission member, the second plane being parallel to the rotation shaft and inclined with respect to the first plane so as to extend by a set distance from a position closer to the distal end side in the axial direction than the proximal end to a distal end side in the axial direction, and at least part of the second plane comes into contact with the inside plane during rotation of the output member to receive the rotation force of the output member; and a third plane connecting a proximal end in the axial direction of the second plane and the first plane of the rotation transmission member, the third plane contacting with a proximal end in the axial direction of the output member when the output member rotates with respect to the rotation transmission member and at least part of the second plane contacts the inside plane, to restrict the rotation transmission member from moving toward the distal end side in the axial direction with respect to the output member.

2. The driving force transmission mechanism according to claim 1, wherein the second plane comprises an end portion configured to receive a rotation force of the output member by contacting the inside plane along the rotation shaft during rotation in one direction of the output member when the first plane is inserted into the through hole so as to face the inside plane.

3. The driving force transmission mechanism according to claim 1, wherein a flexible torque shaft inserted into the insertion portion and coaxially coupled with a distal end in the axial direction of the rotation transmission member.

4. The driving force transmission mechanism according to claim 3, further comprising a driven member disposed in the insertion portion, wherein the distal end in the axial direction of the torque shaft is coupled with a driven member and configured to drive the driven member along with rotation.

5. An endoscope comprising the driving force transmission mechanism according to claim 1.

6. The endoscope according to claim 5, further comprising a spiral structure rotatably provided on an outer circumferential surface of the insertion portion.

7. The driving force transmission mechanism according to claim 1, the rotation transmission member further comprising a receiving surface connecting the first plane and a distal part of the outer circumferential surface of the rotation transmission member.

8. A driving force transmission mechanism for use with an endoscope, the driving force transmission mechanism comprising:

an output member driven by a motor to rotate around a rotation shaft, the output shaft including a through hole along the rotation shaft;

a rotation transmission member inserted into the through hole of the output member from one side of the rotation shaft and configured to receive a rotation driving force around the rotation shaft in a same direction as a direction of the rotation of the output member with the rotation of the output member;

an inside plane provided on an inner surface of the through hole in the output member and extending parallel to the rotation shaft;

a first plane extending to another end in an extending direction of the rotation shaft parallel to the rotation shaft on an outer circumferential surface of the rotation transmission member and part of the first plane faces the inside plane of the output member when the rotation transmission member is inserted into the through hole of the output member;

a second plane provided on the outer circumferential surface of the rotation transmission member, the second plane being parallel to the rotation shaft and inclined with respect to the first plane so as to extend by a set distance from a position closer to one end of the rotation transmission member in the extending direction than an other end of the rotation transmission member, and at least part of the second plane comes into contact with the inside plane during rotation of the output member to receive the rotation force of the output member; and a third plane connecting an end face of the second plane on an other end side of the rotation shaft and the first plane and comes into contact with an end portion on the other end side in the extending direction of the output member when the output member rotates with respect to the rotation transmission member and at least part of the second plane contacts the inside plane, to restrict the rotation transmission member from moving toward the end side with respect to the output member.

9. An endoscope comprising the driving force transmission mechanism according to claim 8, the endoscope comprising:

an insertion portion configured to be inserted into an object; and an operation portion provided proximally relative to the insertion portion;

wherein the drive source is disposed at one of a proximal end portion of the insertion portion or in the operation portion.

10. The driving force transmission mechanism according to claim 8, the rotation transmission member further comprising a receiving surface connecting the first plane and a distal part of the outer circumferential surface of the rotation transmission member.

11. A driving force transmission mechanism for use with an endoscope, the driving force transmission mechanism comprising:

an output member configured to be driven by a motor to rotate around a rotation axis, the output member including a hole along the rotation axis, the hole comprising an inside plane;

a rotation transmission member inserted into the hole and configured to receive a rotation driving force around the rotation axis along with a rotation of the output member, the rotation transmission member comprising:

a first plane configured to extend to a proximal end along the rotation axis on an outer circumferential surface of the rotation transmission member, a part of the first plane contacting with the inside plane of the output member when the output member rotates in a first direction;

a second plane provided on the outer circumferential surface of the rotation transmission member, the second plane being arranged along the rotation axis, the second plane configured to be inclined with respect to the first plane, a proximal end of the second plane is provided distally relative to a proximal end of the rotation transmission member, and at least part of the second plane contacting with the inside plane of the output member when the output member rotates in a second direction opposite to the first direction; and a third plane connecting the proximal end of the second plane and the first plane to contact with a proximal end of the output member when the output member rotates with respect to the rotation transmission member in the second direction to restrict the rotation transmission member from moving distally relative to the output member.

12. The driving force transmission mechanism according to claim 11, wherein the second plane comprises an end portion configured to receive a rotation force of the output member by contacting the inside plane along the rotation shaft during rotation in the second direction when the first plane is inserted into the hole to face the inside plane.

13. The driving force transmission mechanism according to claim 11, wherein a flexible torque shaft inserted into the insertion portion and coaxially coupled with a distal end of the rotation transmission member.

14. The driving force transmission mechanism according to claim 13, further comprising a driven member disposed in the insertion portion, wherein the distal end of the torque shaft is coupled with a driven member and configured to drive the driven member along with rotation.

15. An endoscope comprising the driving force transmission mechanism according to claim 11, the endoscope comprising:
an insertion portion configured to be inserted into an object; and
an operation portion provided proximally relative to the insertion portion;
wherein the drive source is disposed at one of a proximal end portion of the insertion portion or in the operation portion.

16. The endoscope according to claim 15, further comprising a spiral structure rotatably provided on an outer circumferential surface of the insertion portion.

17. The driving force transmission mechanism according to claim 11, wherein a length of the rotation transmission member is longer than a length of the output member.

18. The driving force transmission mechanism according to claim 11, the rotation transmission member further comprising a receiving surface connecting the first plane and a distal part of the outer circumferential surface of the rotation transmission member.

* * * * *